United States Patent
Stoops

(10) Patent No.: US 11,344,592 B1
(45) Date of Patent: *May 31, 2022

(54) FOOD GRADE CANNABIS EXTRACTS AND METHODS FOR THEIR PREPARATION

(71) Applicant: Daniel Hartman Stoops, Portland, OR (US)

(72) Inventor: Daniel Hartman Stoops, Portland, OR (US)

(73) Assignee: Fiji Kava LTD, West End (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/946,321

(22) Filed: Jun. 16, 2020

Related U.S. Application Data

(63) Continuation of application No. 15/902,761, filed on Feb. 22, 2018, now Pat. No. 10,716,819.

(60) Provisional application No. 62/462,190, filed on Feb. 22, 2017.

(51) Int. Cl.
*A61K 36/185* (2006.01)
*A61K 47/10* (2017.01)
*A61K 9/00* (2006.01)

(52) U.S. Cl.
CPC ............ *A61K 36/185* (2013.01); *A61K 47/10* (2013.01); *A61K 9/007* (2013.01); *A61K 9/0095* (2013.01); *A61K 2236/33* (2013.01); *A61K 2236/53* (2013.01)

(58) Field of Classification Search
None
See application file for complete search history.

(56) References Cited

U.S. PATENT DOCUMENTS

| | | | |
|---|---|---|---|
| 9,468,865 B1 | 10/2016 | Young et al. | |
| 9,808,494 B2 | 11/2017 | Barringer | |
| 10,716,819 B2 * | 7/2020 | Stoops | A61K 36/185 |
| 10,738,268 B2 * | 8/2020 | Leo | C12G 3/06 |
| 2006/0088627 A1 | 4/2006 | Bartnick et al. | |
| 2012/0095087 A1 | 4/2012 | Hyatt | |
| 2017/0020944 A1 | 1/2017 | Towle | |
| 2017/0360861 A1 | 12/2017 | Humphreys et al. | |
| 2018/0344661 A1 | 12/2018 | Finley et al. | |

* cited by examiner

*Primary Examiner* — Ralph J Gitomer
(74) *Attorney, Agent, or Firm* — Howard Russell, Attorney at Law

(57) ABSTRACT

Food grade cannabis extracts and methods for their preparation that may reduce or eliminate the anxiety effect that cannabis may have on a user. Embodiments of the methods include providing raw botanical material; providing food grade glycerin; combining the botanical material with the glycerin; blending the botanical material and the glycerin to achieve a homogenous mixture; optionally pre-heating the mixture prior to being agitated; placing the mixture in a sealable container; providing an agitator; securing the container on or within the agitator, agitating the mixture and allowing the mixture to rest at various intervals; heating the mixture and allowing the mixture to cool at various intervals; straining the mixture; pressing the mixture; and then filtering the mixture to remove any remaining particulates to thereby produce a food grade cannabis extract suitable for at least medical use.

16 Claims, 5 Drawing Sheets

FOOD GRADE CANNABIS EXTRACTS AND METHODS FOR THEIR PREPARATION

RELATED APPLICATIONS

This application is a continuation of Non-Provisional patent application Ser. No. 15/902,761 entitled "Food Grade Cannabis Extracts and Methods for Their Preparation" and filed on Feb. 22, 2018, which claims priority to, and the benefit of, U.S. Provisional Application No. 62/462,190 entitled "Methods for Preparing Food Grade Cannabis Extracts" and filed on Feb. 22, 2017, the entire contents of which are incorporated by reference as though fully described herein.

TECHNICAL FIELD

The present disclosure relates generally to botanical extracts and methods for their preparation, and more specifically—but not by way of limitation—to food grade cannabis extracts and methods for preparing the same that may reduce or eliminate the side effect of anxiety that cannabis may have on a user.

BACKGROUND

Cannabis has reportedly provided users with relief from a variety of medical ailments including chronic pain, epilepsy, inflammation, and nausea resulting from chemotherapy. See, for example, Laura M. Borgelt et al., *The Pharmacologic and Clinical Effects of Medical Cannabis*, Pharmacotherapy (2013) 33(2):195-209; Penny F. Whiting et al. *Cannabinoids for Medical Use: A Systematic Review and Meta-Analysis*, JAMA (2015) 313(24):2456-2473, doi:10.1001/jama.2015.6358; Bjorn Jensen et al., *Medical Marijuana and Chronic Pain: A Review of Basic Science and Clinical Evidence*, Curr. Pain Headache Rep. (2015) 19:50, https://doi.org/10.1007/s11916-015-0524-x; and Guillermo Velasco et al., *Towards the Use of Cannabinoids as Antitumour Agents*, Nature Reviews Cancer 12 (2012) 436-444, doi:10.1038/nrc3247, which are hereby incorporated by reference.

To achieve such relief, users have often consumed liquid cannabis extracts as an alternative to smoking cannabis plant material. Current methods have been able to create cannabis extracts from raw cannabis plant material, and have produced concentrated amounts of biologically active compounds, i.e., cannabinoids, terpenes, terpenoids, and flavonoids, or more specifically, tetrahydrocannabinol (THC), cannabidiol (CBD), cannabinol (CBN), cannabichromene (CBG), tetrahydrocannabivarin (THCV), and others. For example, existing methods of extraction have produced cannabis extracts consisting of ninety percent (90%) or greater THC, whereas a cannabis plant from which the extract was derived has only consisted of fifteen percent (15%) or less THC. The resulting cannabis extracts have been more potent by volume than the raw botanical material from which they were derived, and thus users have reportedly experienced comparable effects, or even greater effects, though they have consumed far smaller volumes of cannabis extract than would have otherwise been required to achieve those effects.

Prior art methods for preparing food grade cannabis extracts have involved using solvents such as supercritical—or subcritical—carbon dioxide ($CO_2$), butane ($C_4H_{10}$), liquid propane ($C_3H_8$), and ethanol ($C_2H_6O$). These solvents have often been used to produce cannabis extracts with maximum potency, e.g., they have produced higher concentrations of THC, CBD, or other chemical compounds found in cannabis. However, the prior art methods by themselves have reportedly done little or nothing to reduce or eliminate an undesirable side effect of creating or exacerbating anxiety in a user. Increased anxiety has generally been considered to be an adverse reaction to elevated levels of THC, and this may especially have been a problem for users already having suffered from stress or anxiety. Although not all users have experienced increased anxiety as a result of having consumed cannabis, this undesirable effect has prevented many individuals suffering from medical ailments from being able to comfortably consume cannabis products, and has deterred individuals from consuming cannabis products altogether.

Responsive to the limitations of the prior art, recent trends in the cannabis industry have included preparing cannabis extracts from cannabis strains that have been rich or dominant in CBD, and that have had little to no THC content. The benefit of having prepared extracts from CBD-rich or CBD-dominant strains is that CBD may have counteracted the anxiety effect caused by THC, and consequently may have provided users with relief from certain medical conditions without having created or having exacerbated anxiety. However, cannabis extracts having lower levels of THC may also have been less medically effective than their THC-rich counterparts. For example, scientists have noted that THC has been medically useful because it has had the greatest anti-cancer activity of all cannabis compounds. In either case—whether with cannabis extracts having higher levels of THC that may have induced or increased anxiety in a user, or with cannabis extracts that have had lower levels of THC that has rendered them less medically valuable—the outcome has been that a user may not have experienced optimal or desired results.

Accordingly, there has developed a need for cannabis extracts, and methods for their preparation, that would reduce or eliminate the anxiety effect on a user without requiring the extracts to have a lower THC content.

SUMMARY

In an embodiment of the present teachings, there is provided—a method for preparing a botanical extract comprising the steps of: providing a raw botanical material (such as, for example, cannabis); combining the botanical material with glycerin; blending the botanical material and the glycerin to achieve a homogenous mixture; optionally preheating the mixture; alternately and repeatedly agitating the mixture and then allowing the mixture to rest; alternately and repeatedly heating the mixture and then allowing the mixture to cool; at least substantially separating a liquid component from a solid component of the mixture to produce an extract of the botanical material; and optionally filtering the extract to remove any remaining particulates.

In some embodiments, the step of agitating the mixture may be accomplished by using a motorized agitator, such as but not limited to a gyroscopic agitator, vibrational agitator, drum hoop mixer, tumbler, or any other suitable agitating device. For purposes of this disclosure, "agitation" refers to the action of shaking, stirring, tumbling, or otherwise mixing the mixture. In some embodiments, the step of substantially separating a liquid component from a solid component of the mixture may be accomplished by straining and pressing the mixture, such as by using a tincture press. In some embodiments, the liquid component may be further separated from the solid component of the mixture by adding a step of filtering the extract to remove any remaining particulates therefrom. In some embodiments, the mixture may be agitated and heated at the same time. Likewise, the mixture may be allowed to rest and cool at the same time. In some embodiments, the resulting extract may include no other solvent in addition to the glycerin.

In accordance with another embodiment and aspect of the present teachings, there is provided—a method for reducing anxiety associated with consuming a cannabis product, comprising the steps of: providing a raw cannabis plant material such as, for example, any combination of cannabis leaves, stems, flowers, and roots; providing food grade glycerin; combining the plant material with the glycerin; blending the plant material and the glycerin to achieve a homogenous mixture; optionally pre-heating the mixture; using a motorized agitator to agitate the mixture; allowing the mixture to rest after agitation; using a heat source to heat the mixture to a temperature suitable for decarboxylation of at least one cannabinoid of the plant material; allowing the mixture to cool after heating; straining the mixture to produce an extract of the plant material; and optionally filtering the extract to remove any remaining particulates.

In some embodiments, the mixture may be alternately and repeatedly agitated and then allowed to rest at predetermined intervals over the course of several hours, days, or months—or, the mixture may be continuously agitated over the course of several hours, days, or months, without being allowed to rest until after agitation is complete. Likewise, in some embodiments, the mixture may be alternately and repeatedly heated and then allowed to cool at predetermined intervals over the course of several, hours, days, or months—or, the mixture may be continuously heated over the course of several hours, days, or months, without being allowed to cool until after heating is complete. For example, the mixture may be heated to a temperature or temperatures between approximately 180 and 260 degrees Fahrenheit and then allowed to cool to a temperature or temperatures between approximately 34 and 100 degrees Fahrenheit. In some embodiments, the mixture may be pressed and filtered to separate the extract from any remaining particulates of the plant material.

In accordance with yet another embodiment and aspect of the present teachings, there is provided—a liquid cannabinoid composition comprising at least one cannabinoid and a quantity of food grade glycerin and no other solvent. In some embodiments, the at least one cannabinoid may include at least seventy percent (70%) THC as to potentially maximize THC-related medical benefits for a user of the extract. In other embodiments, the at least one cannabinoid may include at least seventy percent (70%) CBD as to potentially maximize CBD-related medical benefits for a user of the extract. Other embodiments may include any desired combination of cannabis-derived cannabinoids, generally depending on the strain or strains of cannabis from which each extract is prepared. In some embodiments, the glycerin used in the extract may be derived from plant oils as to be suitable for consumption by users having a vegan diet (as opposed to the glycerin that is derived from animal fat).

Thus, methods for preparing food grade extracts from botanical materials, such as cannabis plants and any portion thereof, are provided herein. These methods may reduce, or eliminate, the anxiety effect of cannabis on a user, and at least in some cases regardless of the chemical composition of the cannabis plant(s) from which the extracts are derived. Increased anxiety has been considered to be an adverse reaction to THC and potentially other chemical compounds found in certain strains of cannabis. The methods provided herein utilize a unique combination of glycerin, agitation, and heat to extract biologically active compounds from raw cannabis plant material. The present methods result in food grade cannabis extracts suitable for at least medical use, having any of a number of different chemical compositions, and that reportedly minimize undesirable anxiety effects that cannabis may have on a user.

DETAILED DESCRIPTION

I. General Features

Figure 1:
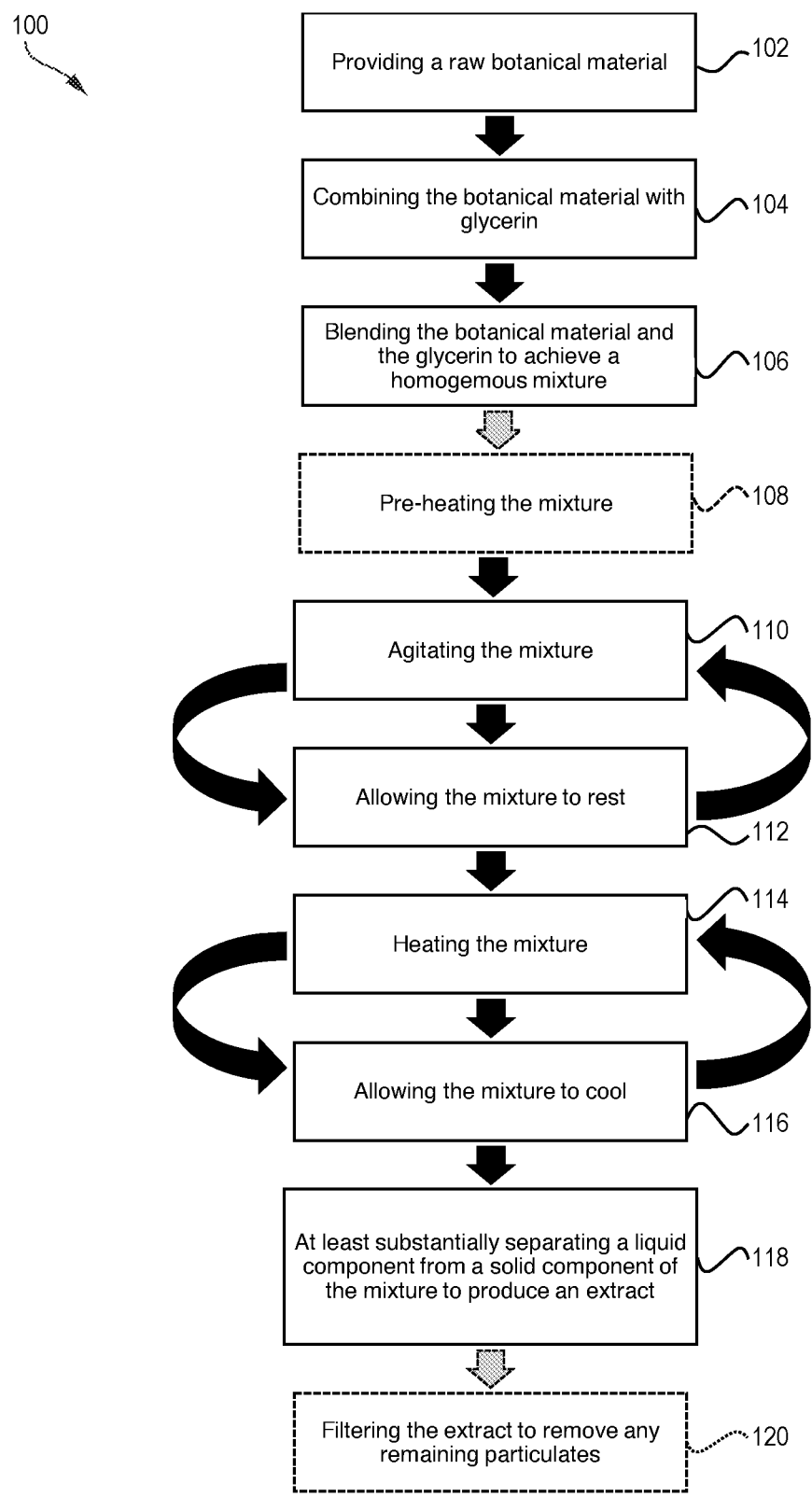
FIG. 1 is a flowchart showing steps of an exemplary method for preparing a food grade botanical extract, according to aspects of the present teachings.

This section describes general features of food grade botanical extracts.

The disclosed botanical extracts include food grade cannabis extracts that may be suitable for at least medical use, which are prepared according to methods capable of potentially reducing or eliminating an undesirable anxiety effect that cannabis may have on a user thereof. As used herein, "food grade" means that a human may ingest up to a specified amount of a particular substance without generally suffering deleterious health effects. Examples of food grade substances include such substances "generally recognized as safe" (GRAS) by the U.S. Food and Drug Administration (FDA). Specifically, food grade substances include those listed under 21 C.F.R. §§ 73, 74, 172, 182, and 184.

A significant benefit to using food grade botanical materials and glycerin is that a user may directly ingest the resulting botanical extract, either by itself or by adding the extract to other ingestible products, such as, for example, coffee, tea, essential oil extracts, and so on; or, the user may vape the extract using a vaporizing device such as a vape pen or similar. In some embodiments, the botanical material may consist of at least one of cannabis leaves, stems, flowers, and roots, or any combination thereof. However, the disclosed extracts and methods for their production may use any raw botanical material or combination of materials for creating extracts that may be fit for human consumption, not limited to cannabis. For purposes of this disclosure, the terms "cannabis extract" and "botanical extract" are not mutually exclusive and may be used interchangeably.

In accordance with an aspect of the present disclosure, an exemplary cannabis extract may be more specifically described as a liquid cannabinoid composition comprising at least one cannabinoid and a quantity of food grade glycerin. In some embodiments, it may be preferable for the glycerin to be the only solvent present in the cannabis extract. Specifically, some embodiments may be completely devoid of conventional solvents that have been used for extracting cannabis, such as—but not limited to—supercritical $CO_2$, butane ($C_4H_{10}$), liquid propane ($C_3H_8$), and ethanol ($C_2H_6O$). The glycerin-only extracts disclosed herein may include glycerin derived from vegetable oils, petroleum, and/or animal fat; however, it may be preferable to use 100% vegetable glycerin so that the extract is suitable for vegan diets.

One of the many benefits to using glycerin as the primary or only solvent in a cannabis extract is due to glycerin preserving the biological viability of the chemical compounds extracted from the raw cannabis plant material, allowing the various compounds to work together to produce a synergy of effects. This is often referred to in the cannabis industry as the "entourage effect." On the other hand, conventional solvents such as supercritical $CO_2$, butane ($C_4H_{10}$), liquid propane ($C_3H_8$), and ethanol ($C_2H_6O$) are more likely to denature many of the chemical compounds found in raw cannabis plant material. As a result, cannabis extracts in which glycerin is the primary or only solvent may provide a greater "entourage effect" than extracts using other types of solvents.

Any strain or combination of strains of cannabis may be used in the disclosed extracts and methods for their production. For example, in some embodiments, the at least one cannabinoid present in each cannabis extract may include at least seventy percent (70%) THC, at least seventy percent (70%) CBD, or any suitable percentage of other cannabis constituents or combinations thereof depending on the desired effect of the extract on a user. Generally, the levels of certain chemical compounds such as THC and CBD of the botanical material determine the corresponding levels of those compounds in the resulting cannabis extract. Thus, a cannabis extract produced from a CBD-dominant strain (such as hemp) may be useful in certain medical applications, whereas a THC-dominant strain may be useful for other applications. Because the disclosed methods may reduce or eliminate the anxiety effect most often associated with an adverse reaction to THC, even THC-rich or THC-dominant strains of cannabis may possibly be extracted and ingested or inhaled as a vapor by a user without creating or increasing anxiety levels of the user.

Generally, the disclosed botanical extracts may have a smooth, syrupy texture and a sweet taste, substantially similar to the texture and taste of pure vegetable glycerin. The extracts may be consumed directly, inhaled as a vapor produced by a vaporizing device, and/or added to beverages and/or foods. In some embodiments, the botanical extracts may be stored and sealed in any suitable vessel (such as, for example, a vessel that is opaque, airtight, and/or made of glass), and may also be refrigerated and/or frozen to prolong their shelf life. The shelf life of any particular botanical extract may depend on the quality of the raw botanical material from which the extract is derived. Additionally, certain cannabinoids, flavonoids, terpenes, and other molecules found in cannabis plant material may degrade faster than others. And, although some embodiments may have a shelf life of one year or longer, with or without refrigeration and/or freezing, a well-stored botanical extract may have a practically indefinite shelf life with little to no degradation. Additionally, although some extracts may be substantially free of any solids or particulates suspended therein, some natural separation and/or settling may occur over time.

II. Production Methods

This section describes methods for preparing botanical extracts, according to aspects of the present teachings. See FIGS. 1-5.

FIG. 1 is a flowchart showing steps of an exemplary method 100 for preparing a food grade botanical extract, according to aspects of the present teachings, comprising: a first step 102 of providing a raw botanical material; a second step 104 of combining the botanical material with the glycerin; a third step 106 of blending the botanical material and the glycerin to achieve a homogenous mixture; an optional fourth step 108 of pre-heating the mixture; a fifth step 110 of agitating the mixture; a sixth step 112 of allowing the mixture to rest; a seventh step 114 of heating the mixture; an eighth step 116 of allowing the mixture to cool; a ninth step 118 of at least substantially separating a liquid component of the mixture from a solid component of the mixture to produce an extract of the botanical material; and an optional tenth step 120 of filtering the extract to remove any remaining particulates.

With respect to the first step 102 of the method 100, the botanical material may consist of any food grade botanical material, such as, for example, cannabis leaves, stems, flowers, and roots, or any combination thereof. In some embodiments, the botanical material may be broken into smaller pieces to facilitate the extraction process. This may be accomplished by cutting, chopping, grinding, and/or manually breaking apart any larger pieces, or by any other appropriate means. For example, in embodiments using cannabis as the botanical material, the cannabis plant material may be ground into uniform pieces having sizes of approximate 1-10 millimeters in length, such as by using a grinder, for ease of mixing with the glycerin in steps 104 and 106. In other embodiments, the plant material may be manually broken into uniform pieces having sizes of approximately ¼ to ½ inch in length.

Additionally, the disclosed methods may be used with botanical materials other than cannabis. For example, certain plants may contain biologically active constituents having powerful antioxidant activities and potentially other medicinal benefits when consumed as an extract by a user. See, for example, Yaejin Woo et al., *Antioxidant Potential of Selected Korean Edible Plant Extracts*, Hindawi: BioMed Research Intl, Vol. 2017, Article ID 7695605.

With respect to the second step 104 of the method 100, the botanical material is combined with a solvent consisting of glycerin, such as but not limited to food grade vegetable glycerin, according to aspects of the present disclosure. In other embodiments, the glycerin may be animal-derived or petroleum-derived glycerin, or may be any combination of the above. Similarly, the glycerin may be organic, not organic, or a combination thereof. In preferred embodiments, however, the glycerin is food grade so that the botanical extract resulting from the disclosed methods may be safe for humans to ingest and/or vape. Glycerin is listed as a "multiple purpose GRAS food substance" under 21 C.F.R. § 172.

In some embodiments, the second step 104 may be performed by first placing the botanical material in a container and then adding the glycerin to the botanical material in the container. However, it is immaterial in what order the botanical material and the glycerin are combined. In some embodiments, a mathematical equation may be used to determine an appropriate ratio of cannabis plant material to solvent, based on a target potency of the cannabis extract. For example, an appropriate ratio may be approximately 2.5-3 grams of botanical material to 1 fluid ounce of the glycerin. The methods disclosed herein may be scalable, i.e., they may be performed on a small scale or on an industrial level, depending on the starting quantities of the botanical material and the glycerin—as well as the size and power of the apparatuses used for blending, heating, agitation, and other steps of the method 100 that may require the use of machinery.

The container may be any vessel suitable for the combining of the botanical material and the glycerin therein, such as, for example, a mixing bowl, a mixing drum, or a mixing tank—generally depending on the quantity of the material and the glycerin needing to be contained. In some embodiments, it may be preferable for the container used during this second step 104 to be made from a food grade material, as to preserve the food safety of the extract that will result from the method 100. In some embodiments, it may also be preferable for the container to be sealable so that the container may be sealed during the fifth step 110 (i.e., agitating the mixture), and to be heat-safe so that the container may withstand a heat source applied thereto during the seventh step 114 (i.e., heating the mixture). However, any number of different containers may be used during each step.

With respect to the third step 106 of the method 100, the combination of the glycerin and the botanical material resulting from the second step 104 may be blended or otherwise mixed together to create a homogenous mixture. In some embodiments, the homogenous mixture may be achieved by stirring the combination of the botanical material and the glycerin with a suitable mixing instrument such as but not limited to a spatula or spoon. Alternatively, or additionally, the homogenous mixture may be achieved by using a motorized blender, such as—but not limited to—an industrial blending machine. Generally, the mixture may be deemed homogenous when it is uniform, i.e., the solid botanical material and the liquid glycerin are evenly distributed throughout the mixture.

With respect to the optional fourth step 108, in some but not all embodiments, the mixture may be heated prior to being agitated, during a "pre-agitation heating phase" or—more simply put—the mixture may be "pre-heated." Pre-heating the mixture may facilitate the transfer of chemical compounds from the botanical material to the solvent, thereby increasing the potency of the resulting botanical extract. For example, the mixture may be pre-heated to a temperature of approximately 80-240 degrees Fahrenheit prior to agitating the mixture. The temperature at which to pre-heat the mixture may depend on the type of botanical material used. For example, a strain of cannabis that is rich in CBD may be pre-heated to 240 degrees Fahrenheit for the substantially complete decarboxylation of CBD and potentially other cannabis constituents of the botanical material. Because the botanical material may include various different strains of cannabis, the ideal temperature during the pre-heating step may vary.

With respect to the fifth step 110 of agitating the mixture and the sixth step 112 of allowing the mixture to rest, these two steps may be performed alternately and repeatedly (as indicated by the bold arrows in FIG. 1). That is, the mixture may be agitated, allowing to rest, agitated again, allowed to rest again, and so on—at predetermined intervals over the course of several hours, days, or months. Likewise, the seventh step 114 of heating the mixture and the eighth step 116 of allowing the mixture to cool may also be performed alternately and repeatedly (as indicated by the bold arrows in FIG. 1). More specifically, the mixture may be heated, allowed to cool, heated again, allowed to cool again, and so on—also at predetermined intervals over the course of several hours, days, or months. Generally, the more times the mixture is alternately and repeatedly agitated and allowed to rest, and alternately and repeatedly heated and allowed to cool, the more potent the resulting extract may be. Accordingly, other embodiments may provide for the continuous agitation and heating of the mixture to potentially produce a more potent extract.

The seventh step 114 and eighth step 116 comprise a "post-agitation heating and decarboxylation phase" of the method 100. In some embodiments, this phase may cause the resulting extract to be orally active. Specifically, a heat source may be applied to the mixture during the seventh step 114, the heat source being capable of heating the mixture to a temperature of approximately 180-260 degrees Fahrenheit. The mixture may be heated in any suitable manner. For example, in some embodiments, the mixture may be removed from the agitator and placed on a stovetop, in a stove, or in proximity to any other suitable heat source—such as while being contained in a heat-safe container. In other embodiments, the mixture may be placed within a heat-safe container and submerged in a water bath. In yet other embodiments, the agitator may include a heat source and therefore the mixture may not need to be removed from the agitator to be heated.

In some embodiments, the mixture may be heated to a temperature such as 200 degrees Fahrenheit, using any suitable heat source. In some embodiments, the heat source may be automated to turn on and off at predetermined intervals, by an internal or external on/off switch. Alternatively, the heat source may be manually turned on and off at desired intervals. Examples of suitable heat sources include, without limitation, stovetops and industrial ovens. Additionally, the mixture may be heated at predetermined intervals such that the mixture is heated to a certain temperature for a number of minutes or hours, and then allowed to cool to a certain temperature for a number of minutes or hours, over the course of several hours, days, or months. For example, in some embodiments, the mixture may be heated to a suitable temperature for 3.5 hours and then cooled to below 40 degrees Fahrenheit (i.e., a standard refrigerator temperature) for 12-36 hours. These steps may be repeated one or more times to achieve a desired result.

For another example, the mixture may be heated to 200 degrees Fahrenheit for 60 minutes, allowed to cool to 100 degrees Fahrenheit for 30 minutes, heated back to 200 degrees Fahrenheit for 120 minutes, allowed to cool to 100 degrees Fahrenheit for 60 minutes, followed by a 12-hour inactive period (during which the mixture is left alone), then heated again to 200 degrees Fahrenheit for 240 minutes. The temperature to which the mixture should be heated may vary between intervals, and may depend on the strain or strains of cannabis used. In a preferred embodiment, the mixture may be heated to a temperature suitable for decarboxylation of at least one cannabinoid of the plant material. For example, CBD-rich strains of cannabis may be heated to approximately 240 degrees Fahrenheit for maximum transfer of its constituents. Other strains of cannabis and combinations thereof may be best suited for other temperatures within the approximately 180-260 degree Fahrenheit range.

With respect to the ninth step 118 of the method 100, the liquid component of the mixture may be at least substantially separated from the solid component of the mixture by straining and/or pressing the mixture, such as by using a tincture press. In some embodiments, the mixture may be strained after the post-agitation heating and decarboxylation phase is complete, without allowing the mixture to cool. For example, the mixture may be removed from the heat source and immediately placed within the tincture press. In some embodiments, the tincture press may include a cheesecloth liner, mesh liner, or other suitable porous material; a porous inner vessel; and a solid outer vessel. In such embodiments, the mixture may be placed within the porous inner cylinder that is lined with cheesecloth, and then "pressed" as to strain a liquid portion of the mixture away from a solid portion of the mixture. The liquid portion of the mixture is the botanical extract. The extract may then flow out of an aperture in the solid, outer vessel to be collected. However, other embodiments may include a device that achieves a similar result without necessarily being a tincture press specifically.

In some embodiments, the botanical extract may have little to no remaining particulates after completing the ninth step 118 of the method 100. Accordingly, the method 100 may be complete at this time. However, other embodiments may require the otherwise optional tenth step 120 of filtering the extract to remove any remaining particulates therefrom. The extract may be filtered in any suitable manner, such as, for example, by using a three-step filtering process. For example, a first filtering step may be to filter the extract through a 175-micron filter, a second filtering step may be to filter the extract through a 100-micron filter, and a third filtering step may be to filter the extract through a 50-micron filter. Other embodiments may include only one filtering step, four filtering steps, or any suitable number of filtering steps for removing remaining particulates from the extract. Additionally, other embodiments may include filters having other suitable micron ratings.

Additionally, in some embodiments, the mixture may be heated and/or agitated again after the tenth step 120 of filtering the mixture. For example, in embodiments having CBD-rich plant material, it may be desirable to first filter the mixture using a 250-micron filter, and then re-filter the mixture using a 190-micron filter during the tenth step 120. After that, it may be advantageous to heat the mixture again to approximately 240-260 degrees Fahrenheit to thereby ensure complete decarboxylation of the cannabinoid(s) contained in the plant material. Accordingly, the steps of the method 100 may be reordered and/or repeated in any suitable manner.

Figure 2:
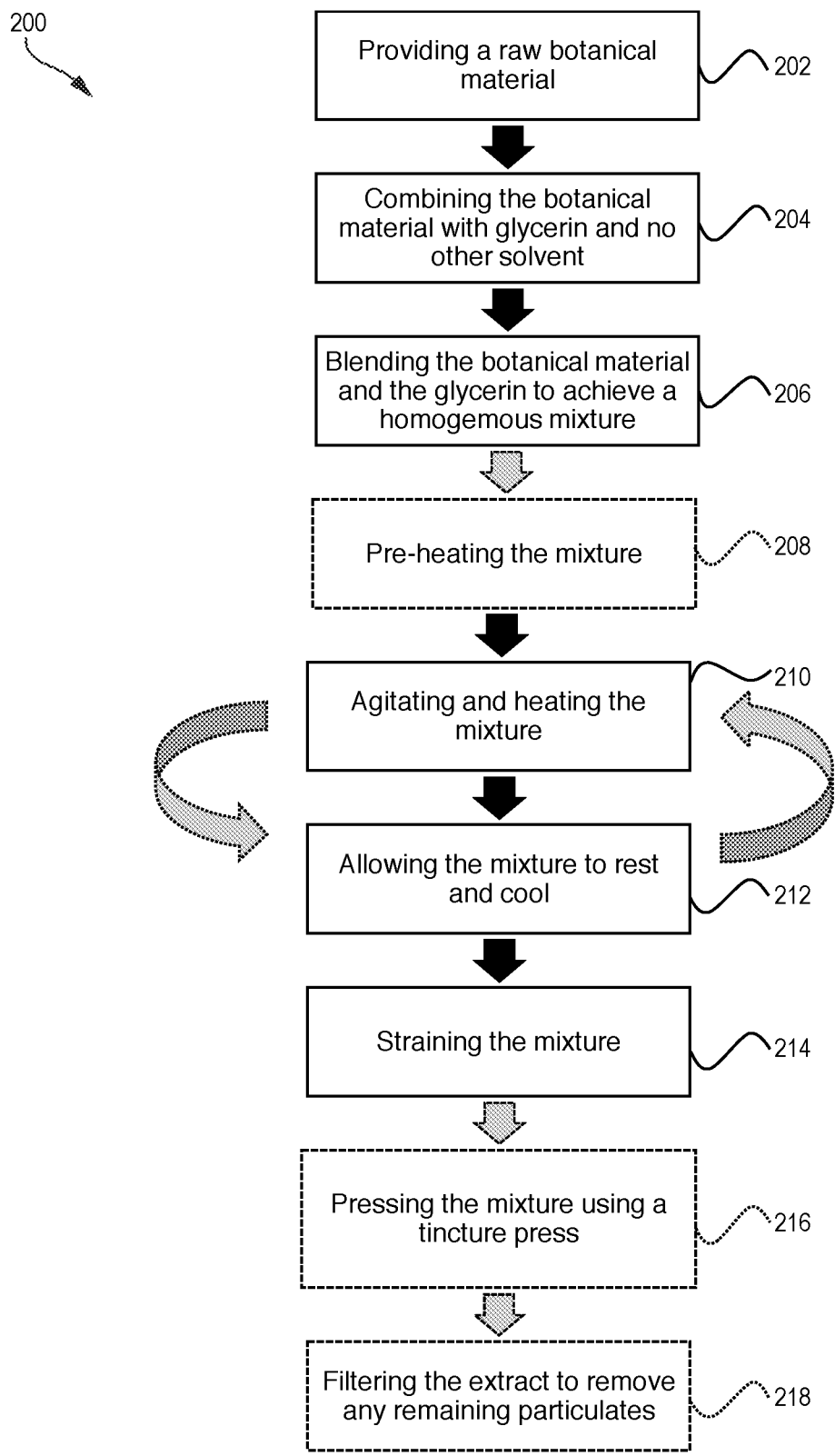
FIG. 2 is a flowchart showing steps of an alternative method for preparing a food grade botanical extract, according to aspects of the present teachings.

FIG. 2 is a flowchart showing steps of an alternative method 200 for preparing a food grade botanical extract, according to aspects of the present teachings, comprising: a first step 202 of providing a raw botanical material, such as but not limited to the leaves, stems, flowers, and/or roots of a cannabis plant; a second step 204 of combining the botanical material with the glycerin—and, in some embodiments, with no other solvent; a third step 206 of blending the raw botanical material and the glycerin to achieve a homogenous mixture; an optional fourth step 208 of pre-heating the mixture; a fifth step 210 of concurrently agitating and heating the mixture; a sixth step 212 of concurrently allowing the mixture rest and cool; a seventh step 214 of straining the mixture; an optional eighth step 216 of pressing the mixture, such as by using a tincture press, to further separate a liquid component of the mixture from a solid component of the mixture; and an optional ninth step 218 of filtering the extract to remove any remaining particulates therefrom.

Several steps of the method 200 may be substantially similar to the steps of the method 100. However, with respect to the fifth step 210 of the method 200, in some embodiments, the mixture may be advantageously heated while being agitated. For example, the mixture may be heated to between approximately 180 and 260 degrees Fahrenheit during agitation. This may be accomplished, for instance, by using a motorized agitator that includes a suitable heat source. Additionally, with respect to the sixth step 212 of the method 200, the mixture may—in some embodiments—be advantageously allowed to cool to while also being allowed to rest between agitation steps. One advantage of combining the agitating and heating steps of the method 200, as opposed to completing these steps separately, may be to reduce the number of hours, days, or months that may be required to produce a botanical extract having a desired potency. The same advantage may apply to combining the resting and cooling steps of the method 200.

For example, the mixture may be allowed to cool to between approximately 34 and 100 degrees Fahrenheit while being allowed to rest before optionally repeating the step 210 of re-agitating and re-heating the mixture. As indicated by the dashed arrows pointing to and from the steps 210 and 212, the method 200 need not require the mixture to be re-agitated and/or re-heated. That is, in some embodiments, the mixture may be heated and/or agitated continuously over the course of several hours, days, and/or months. As discussed in further detail above, the increasing the amount of time that the mixture is heated and/or agitated may thereby increase the potency of the resulting botanical extract.

Figure 3:
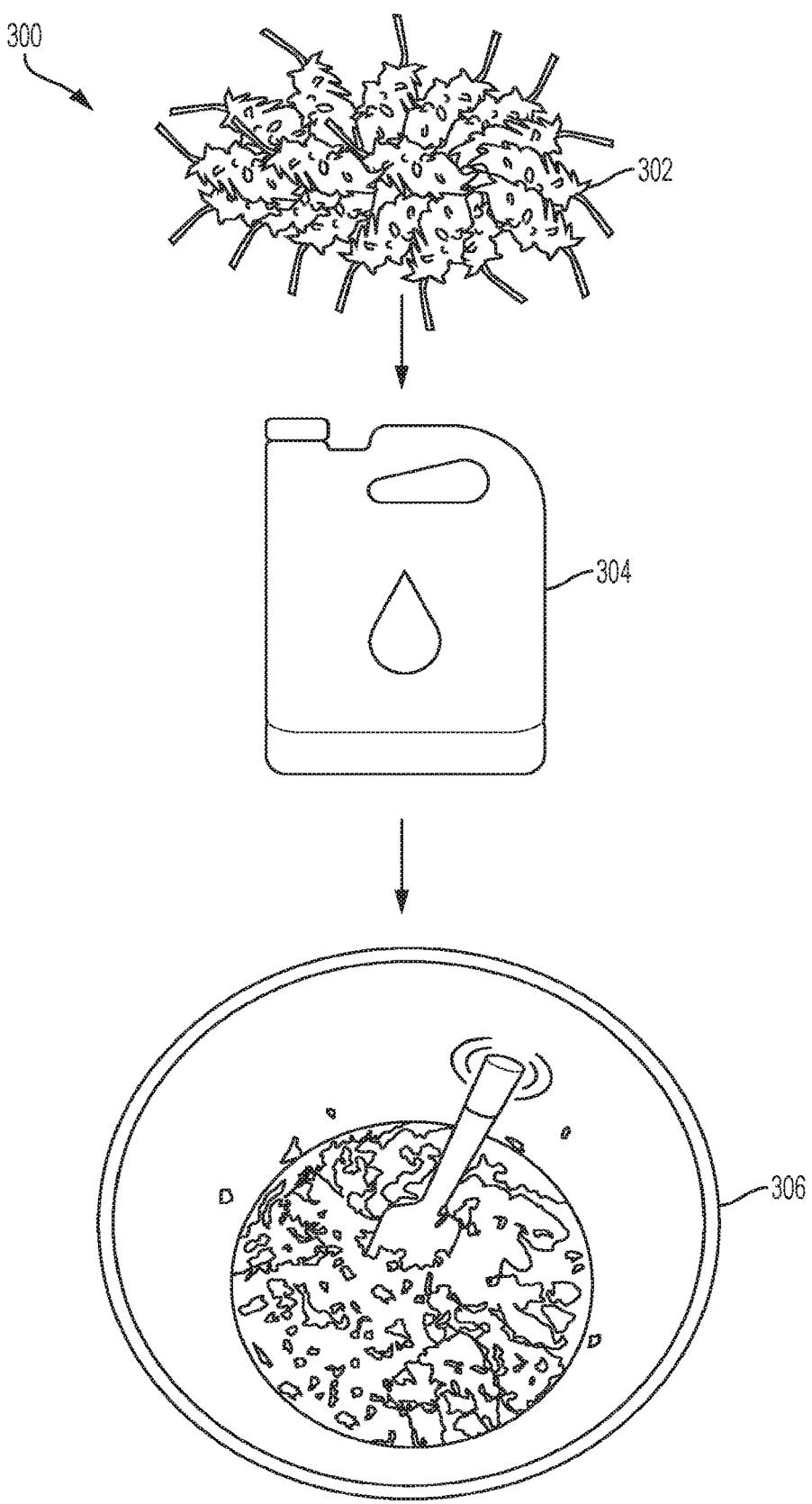
FIGS. 3-5 show a schematic, high-level visual representation of an exemplary method for preparing a food grade cannabis extract, according to aspects of the present teachings.
Figure 4:
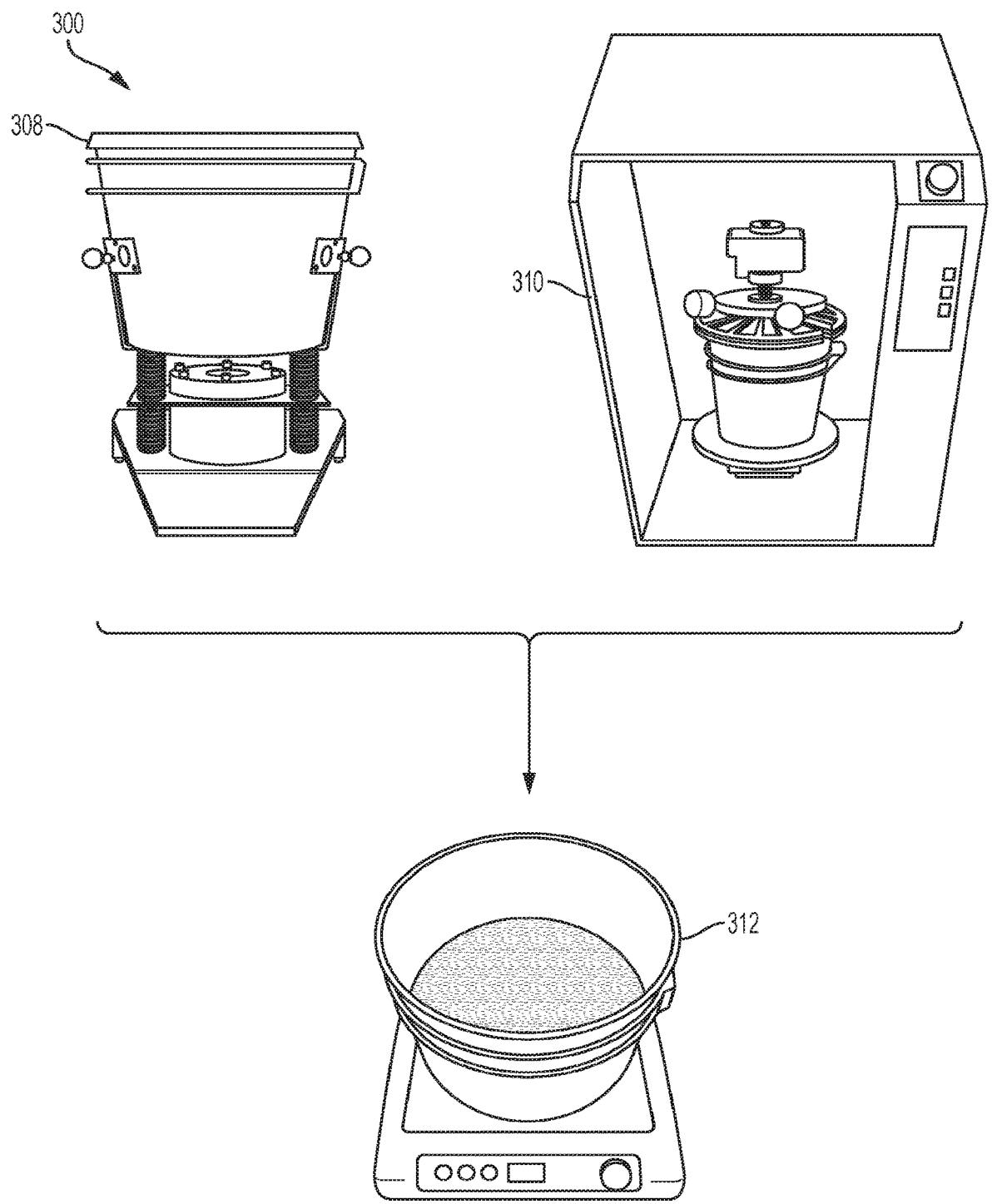
Figure 5:
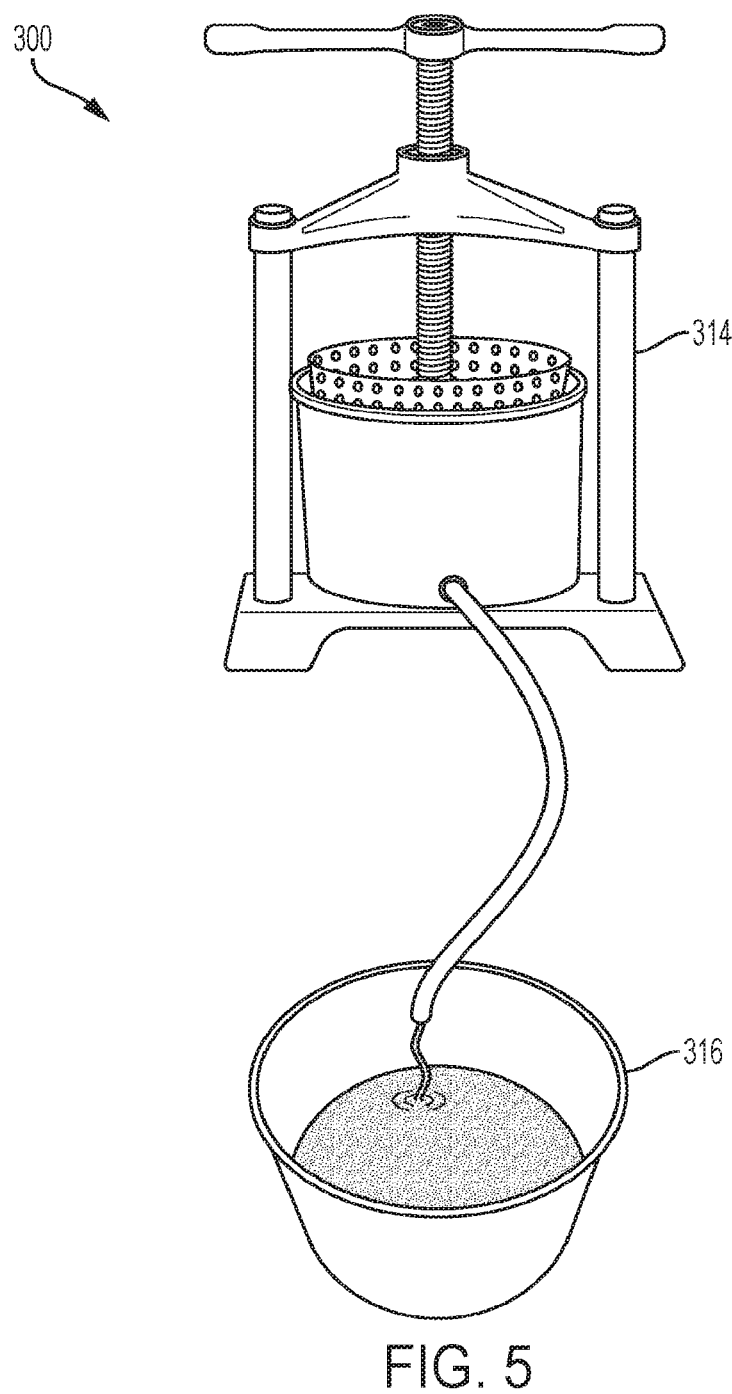

FIGS. 3-5 show a schematic, high-level visual representation of an exemplary method 300 for preparing food grade cannabis extracts, according to aspects of the present teachings. As shown in FIG. 3, the method 300 comprises a first step 302 of providing a raw cannabis plant material, such as cannabis leaves, stems, flowers, and/or roots; a second step 304 of providing food grade glycerin, preferably derived from vegetable oils; and a third step 306 of combining the plant material with the glycerin and blending the two to achieve a homogenous mixture. As shown in FIG. 3, the plant material and the glycerin may be blended together in a sealable container using any suitable mixing instrument, such as but not limited to a spatula. Additionally, the plant material and the glycerin may be blended by hand as shown, and/or by use of a motorized blender.

As shown in FIG. 4, the method 300 also comprises a fourth step 308 or, alternatively, a fourth step 310 of placing the sealable container of the mixture upon or within a motorized agitator. For example, the fourth step 308 may utilize a vibrational agitator, and/or the alternative fourth step 310 may utilize a gyroscopic agitator. In some embodiments, it may be desirable to use both vibrational and gyroscopic agitation during the fourth step(s) 308 and/or 310. As shown in FIG. 4, the vibrational agitator of the fourth step 308 may include a platform on which to place the sealable container of the mixture, and a means to secure the container to the platform. Accordingly, the container may be sealed to fully contain the mixture during agitation. The same sealable container may be used with the gyroscopic agitator in the alternative fourth step 310 of method 300.

Although FIG. 4 shows a vibrational agitator and a gyroscopic agitator, other embodiments may include any suitable type(s) of motorized agitator that further homogenizes the mixture after the third step 306 of blending the mixture, such as—but not limited to—a drum hoop mixer and/or a tumbler. In some embodiments, it may be preferable to use a food grade and/or heat safe container such as a cooking pot made of stainless steel, or the like.

In some embodiments, the mixture may be agitated at predetermined intervals such that the mixture is agitated at a number of minutes and at rest for a number of minutes for a number of hours each day, over the course of several days or months. In some embodiments, the agitator may be automated to turn on and off at predetermined intervals, by an internal or external on/off switch. Alternatively, the agitator may be manually turned on and off at desired intervals. For example, the agitator may run for 3-5 minutes, turn off for 13-15 minutes, and repeat for 10-12 hours a day for 30 days. The number of days may vary depending on the size, power, and durability of the agitator. Generally, increasing the amount of agitation may increase the potency of the resulting botanical extract.

Also, as shown in FIG. 4, embodiments of the method 300 may additionally include a fifth step 312 of heating the mixture. The mixture may be heated in any suitable manner, such as by placing the mixture on a stove, in an oven, or otherwise applying a heat source to the mixture. In a preferred embodiment, the heat source may be capable of heating the mixture to a temperature of approximately 180-260 degrees Fahrenheit, the exact temperature of which may correspond to the optimal temperature for transferring the cannabis constituents of the botanical material to the glycerin and/or to complete decarboxylation of its cannabinoid(s). Because the botanical material may include various different strains of cannabis, the optimal temperature for any given embodiment may vary.

As shown in FIG. 5, the method 300 further comprises a sixth step 314 of straining and pressing the cannabis extract using an apparatus such as a tincture press; and a seventh step 316 of collecting the cannabis extract in a receptacle. The extract may be collected in any suitable manner. For example, the extract may flow out of an aperture in the outer vessel of the tincture press and through a tube such as a rubber hose, to be collected in the receptacle. In other embodiments, the liquid may flow directly out of the aperture and into the receptacle, with or without the use of a funnel. The receptacle may be any suitable container made of any suitable material, such as but not limited to a mixing bowl, a cooking pot, a glass jug, and so on. The resulting extract may be immediately ingested and/or inhaled as a vapor by a user, stored at room temperature for later consumption, refrigerated or frozen to prolong shelf life, delivered to a cannabis dispensary, and/or travel along any other suitable path(s) before reaching an end user.

III. Advantages, Features, Benefits

The different embodiments of food grade botanical extracts and methods for their preparation described herein may provide several advantages over previous extracts and related methods. Perhaps most notably, the illustrative embodiments described herein provide a solution to the problem of users who experience anxiety as a result of consuming THC-rich or THC-dominant strains of cannabis being unable to enjoy the medical benefits of THC. Specifically, a user may consume the cannabis extract resulting from the disclosed methods of preparation possibly without suffering from increased anxiety that may result from an adverse reaction to THC (or any other anxiety-inducing chemical compounds that may be present in certain strains of cannabis). Thus, extracts disclosed herein may be produced from THC-rich or THC-dominant strains of cannabis—thus allowing a user to enjoy the reported medical benefits of THC-rich or THC-dominant strains of cannabis without suffering from the side effect of increased anxiety.

Additionally, and among other benefits, illustrative embodiments described herein allow for relatively low manufacturing costs and are relatively safe, as opposed to conventional methods that may require high pressures, expensive equipment, and a steep operational learning curve to achieve a potent cannabis extract (such as, for example, using supercritical $CO_2$ extraction). Further, methods disclosed herein that use glycerin as the only solvent may provide an added benefit of preserving the biological viability of the chemical compounds extracted from raw cannabis plant material, as opposed to conventional solvents such as supercritical $CO_2$, butane ($C_4H_{10}$), liquid propane ($C_3H_8$), and ethanol ($C_2H_6O$), which are more likely to denature many of the chemical compounds found in raw cannabis. No known methods can produce these results, particularly in conjunction with the remarkable benefit of reducing or completely eliminating the side effect of increased anxiety in a user.

Accordingly, the illustrative embodiments described herein may be particularly useful for users who seek to benefit from the medical use of cannabis, and more particularly, THC. However, not all embodiments described herein provide the same advantages or the same degree of advantage. For example, the botanical extracts described herein may utilize raw botanical material other than cannabis, and the methods for preparing botanical extracts described herein may utilize any strain—or combination of strains—of raw cannabis plant material irrespective of their THC content. Additionally, the disclosed extracts and methods for preparing the same may provide the same or similar medical benefits for users who may not experience increased anxiety as a result of ingesting, vaping, or otherwise consuming THC.

IV. Conclusion

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only, and do not constitute a characterization of any claimed invention. The subject matter of the invention(s) includes all novel and nonobvious combinations and subcombinations of the various elements, features, functions, and/or properties disclosed herein. The following claims particularly point out certain combinations and subcombinations regarded as novel and nonobvious. Invention(s) embodied in other combinations and subcombinations of features, functions, elements, and/or properties may be claimed in applications claiming priority from this or a related application.

What is claimed is:

1. A method for preparing a food grade cannabis extract, comprising the steps of:
   providing a raw cannabis material;
   combining the raw cannabis material with glycerin;
   blending the raw cannabis material and the glycerin to achieve a homogenous mixture without heating the mixture;
   agitating the mixture continuously for approximately two weeks without heating the mixture and allowing the mixture to rest after agitation;
   heating the mixture to at least 203 degrees F. for approximately 8 hours and allowing the mixture to cool after heating;
   separating a liquid component containing extracted cannabinoids from a solid component of the mixture to produce an extract of the raw cannabis material containing cannabinoids by a three-step microfiltration process;
   wherein the three-step microfiltration process utilizes a first filter with a size of approximately 250 microns, followed by a second filter with a size of approximately 190 microns, followed by a third filter with a size of approximately 100 microns, and recovering the liquid component containing extracted cannabinoids;

wherein the raw cannabis material and the glycerin are combined at a ratio of approximately 2.5-3 grams of material per 1 oz of glycerin.

2. The method according to claim 1, wherein glycerin is the only solvent used in the process.

3. A method for preparing a food grade cannabis extract, comprising the steps of:

providing a raw cannabis material;

combining the raw cannabis material with glycerin;

blending the raw cannabis material and the glycerin to achieve a homogenous mixture without heating the mixture;

agitating the mixture continuously for approximately two weeks without heating the mixture and allowing the mixture to rest after agitation;

heating the mixture to approximately 203 degrees F. for approximately 8 hours and allowing the mixture to cool after heating;

separating a liquid component containing extracted cannabinoids from a solid component of the mixture to produce an extract of the raw cannabis material containing cannabinoids by a two-step microfiltration process;

wherein the two-step microfiltration process utilizes a first filter with a size of approximately 175 microns, followed by a second filter with a size of approximately 100 microns, and recovering the liquid component containing extracted cannabinoids.

4. The method according to claim 3, wherein agitating the mixture further comprises the steps of placing the mixture in a sealable container, sealing the container, and placing the container upon a motorized agitator.

5. The method according to claim 3, wherein separating the liquid component from the solid component includes straining and pressing the mixture.

6. The method according to claim 3, wherein the extract does not include any solvent other than the glycerin.

7. The method of claim 3 wherein the raw cannabis material and the glycerin are combined at a ratio of approximately 2.5-3 grams of raw cannabis material per 1 oz of glycerin.

8. The method of claim 7 wherein glycerin is the only solvent used in the process.

9. A method for preparing a food grade cannabis extract, comprising the steps of:

providing a raw cannabis material;

combining the raw cannabis material with glycerin;

blending the raw cannabis material and the glycerin to achieve a homogenous mixture without heating the mixture;

agitating the mixture continuously for at least 7 days without heating the mixture and allowing the mixture to rest after agitation;

heating the mixture to at least 203 degrees F. for approximately 8 hours and allowing the mixture to cool after heating;

separating a liquid component containing extracted cannabinoids from a solid component of the mixture to produce an extract of the raw cannabis material containing cannabinoids by a three-step microfiltration process;

wherein the three-step microfiltration process utilizes a first filter with a size of approximately 250 microns, followed by a second filter with a size of approximately 190 microns, followed by a third filter with a size of approximately 100 microns, and recovering the liquid component containing extracted cannabinoids.

10. The method according to claim 9, wherein agitating the mixture further comprises the steps of placing the mixture in a sealable container, sealing the container, and placing the container upon a motorized agitator.

11. The method according to claim 9, wherein separating the liquid component from the solid component includes straining and pressing the mixture.

12. The method according to claim 9, wherein the extract does not include any solvent other than the glycerin.

13. The method of claim 9 wherein the raw cannabis material and the glycerin are combined at a ratio of approximately 2.5-3 grams of raw cannabis material per 1 oz of glycerin.

14. The method of claim 13 wherein glycerin is the only solvent used in the process.

15. The method of claim 9 wherein the mixture is agitated for approximately 10 days.

16. The method of claim 9 wherein the mixture is agitated for approximately 12 days.

* * * * *